(12) United States Patent
Kesling

(10) Patent No.: US 7,780,442 B2
(45) Date of Patent: *Aug. 24, 2010

(54) BONDABLE ORTHODONTIC APPLIANCE WITH A POLYMER RESIN BONDING BASE

(76) Inventor: Andrew C. Kesling, 1753 S. 100 W., LaPorte, IN (US) 46350

( * ) Notice: Subject to any disclaimer, the term of this patent is extended or adjusted under 35 U.S.C. 154(b) by 1701 days.

This patent is subject to a terminal disclaimer.

(21) Appl. No.: 10/695,695

(22) Filed: Oct. 29, 2003

(65) Prior Publication Data

US 2004/0086824 A1   May 6, 2004

Related U.S. Application Data

(63) Continuation of application No. 10/224,770, filed on Aug. 21, 2002, now Pat. No. 6,685,468.

(51) Int. Cl.
*A61C 7/00* (2006.01)
(52) U.S. Cl. ............................................. 433/9
(58) Field of Classification Search .................... 433/9, 433/8, 10, 15, 17
See application file for complete search history.

(56) References Cited

U.S. PATENT DOCUMENTS

| 3,250,003 | A | * | 5/1966 | Collito | 433/9 |
| 3,345,745 | A | * | 10/1967 | Muller | 433/9 |
| 3,936,939 | A | * | 2/1976 | Faunce | 433/9 |
| 3,964,165 | A | | 6/1976 | Stahl | |
| 4,200,980 | A | | 5/1980 | Johnston | |
| 4,575,337 | A | * | 3/1986 | Fujita | 433/8 |
| 5,098,288 | A | | 3/1992 | Kesling | |
| 5,263,859 | A | | 11/1993 | Kesling | |
| 5,271,733 | A | | 12/1993 | Chikami et al. | |
| 5,441,408 | A | * | 8/1995 | Moschik | 433/8 |
| 5,890,892 | A | | 4/1999 | Lemchen | |

OTHER PUBLICATIONS

TP Orthodontics, Inc. Product Catalog (1998), p. 49.

* cited by examiner

*Primary Examiner*—Ralph A Lewis
(74) *Attorney, Agent, or Firm*—Lloyd L. Zickert

(57) ABSTRACT

An orthodontic appliance of the bracket or tube type for bondable mounting on a tooth including an appliance body having a buccal/labial archwire receiving side and a lingual side and a polymer resin bonding base molded to the lingual side such that at least part of the body is embedded in the base, and wherein the base may include openings for receiving an auxiliary or a secondary archwire.

5 Claims, 4 Drawing Sheets

BONDABLE ORTHODONTIC APPLIANCE WITH A POLYMER RESIN BONDING BASE

This application is a continuation of my application Ser. No. 10/244,770, filed Aug. 21, 2002, now U.S. Pat. No. 6,685,468.

This invention relates in general to an orthodontic appliance for bondable mounting on a tooth including a body and a polymer resin bonding base molded to the body, wherein the base includes an opening for receiving the arm of an auxiliary or a secondary archwire, and also to an orthodontic appliance for mounting on a tooth including a metal orthodontic body and a polymer resin bonding base bonded to the body.

BACKGROUND OF THE INVENTION

Heretofore it has been well known to provide a bondable orthodontic appliance for mounting on a tooth, wherein the appliance includes a body and a bonding base attached thereto wherein the body includes an opening for receiving an arm of an auxiliary such as an uprighting spring.

It is also well known to provide bondable orthodontic appliances for mounting on teeth, such as brackets with or without vertical openings or slots. In the profession, the demand for brackets with or without vertical openings or slots is about equal.

It has also been well known to provide metal orthodontic brackets having bodies with vertical slots and with laminated mesh bonding pads or bases attached to the bodies. These laminated mesh bonding pads or bases include a shield or foil of metal laminated to a wire mesh by a sintering process wherein the foil at the periphery is turned over the periphery of the mesh. Such pads or bases are then attached to the brackets.

It is also known to investment cast metal brackets with integral bonding pads or bases wherein such brackets would in some instances include vertical slots or openings.

Further, it is also been known to use a plastic base on a ceramic bracket as disclosed in U.S. Pat. Nos. 5,098,288 and 5,263,859 to facilitate removal of a bracket bonded to a tooth. The latter patent also teaches adhesively securing a bracket to a preformed plastic base where aligning grooves formed in the bracket and the plastic pad define an opening for receiving an auxiliary.

It has also been known as marketed by TP Orthodontics, Inc. of LaPorte, Ind., to provide a ceramic bracket having a ceramic body with a vertical opening or slot for receiving an anchoring arm of an auxiliary and having a heat-cured plastic bonding pad molded to the body of the bracket. These brackets are manufactured under the trademark MXi, which is a trademark of TP Orthodontics, Inc. The bodies of these brackets have been provided with and without vertical openings or slots.

With respect to the use of ceramic brackets by orthodontists, the demand for brackets with vertical slots about equals the demand for brackets without vertical slots, as above mentioned. This requires the manufacturer to have molds for making each of the types of brackets in order to satisfy the demand. From time to time new molds need to be made in order to produce quality brackets, and such molds are quite expensive. With respect to the MXi brackets made by TP Orthodontics, after the bracket body is molded, the wafer or plastic bonding base of a polymer resin is then molded onto the bracket. Accordingly, the polymer resin base is added as a bonding pad following the molding of the ceramic bracket body.

The advent of light-cure adhesive for bonding appliances to teeth has greatly benefitted orthodontists in reducing chair time, easing chairside use by eliminating the need to mix two or more components, allowing unlimited working time because the adhesive does not set up until exposed to light. However, unlike chemical cure adhesives, light-cure adhesives do not cure in the dark. Heretofore, most brackets have metal bonding bases, and when using light-cure adhesive, the curing requires directing light at the base/tooth enamel interface. In order to get optimum curing for the strongest possible bond between metal bonding bases, light must be directed toward the mesial, distal, occlusal and gingival edges of the bonding base to cure the exposed edges of the adhesive. However, the adhesive at the center of the base does not cure because light never reaches the center.

SUMMARY OF THE INVENTION

The bondable orthodontic appliance of the present invention eliminates the need to form two different appliance bodies having a bonding base or pad attached to the bodies when desired to produce brackets with or without openings or slots extending in any direction opposite to the archwire receiving side of the appliance. More particularly, a slot or opening behind the archwire receiving part of the appliance can be formed in the polymer base molded to the body of the appliance for receiving an arm of an auxiliary or a secondary archwire, whether the appliance is a bracket or a molar tube. Further the bracket may be made of ceramic, metal or plastic. In each case where the body of the appliance is a bracket or a tube, the body of the appliance would be made without any vertical, horizontal or diagonal opening and that opening would then be formed in the polymer base during molding the base onto the body of the appliance. Thus, where brackets would be provided of ceramic material, only a single mold would be needed to make the ceramic bracket body, as where an opening is desired it would be formed in the base. It will be appreciated that one or more openings may be provided to extend vertically, horizontally, or diagonally.

In an orthodontic appliance having a metal appliance body, the invention provides the advantage of only needing to form a single metal body and then thereafter molding an optically clear or translucent bonding pad or base to the body with or without vertical, horizontal or diagonal openings. Since the base is light-permeable, it allows light to reach further under the base to produce a stronger bond. There is no need to illuminate the edges of the base as the light may be directed on top of the base, thereby significantly reducing curing time. Preferably, the bonding face of the base has a meshlike architecture to provide better mechanical interlock.

Additionally, by incorporating a polymer resin bonding pad or base with the metal body of an appliance, and particularly to a bracket or tube where no vertical, horizontal or diagonal slot or opening is needed in the base, the in-out compensation and profile of the bracket or tube is significantly reduced as the bracket or tube body is partially embedded in the polymer resin base rather than being attached on top of the base as when using a metal mesh base. A lower profile substantially reduces the chances of occlusal interference and bond failures, as well as improving hygiene and tissue health. A bondable tube also eliminates the problems associated with tubes mounted on bands. And where light-cure adhesive is used to bond the appliance to a tooth, the polymer resin base being translucent or optically clear, allows the curing light to penetrate beneath the appliance body to enhance the bonding strength.

Further, the number of steps required for making such a bracket or tube with a resin base are substantially less than the number of steps needed to make a bracket or tube with a metal bonding pad or base.

Moreover, the use of an optically clear or translucent polymer base on a bondable metal appliance body reduces the amount of metal exposed thereby greatly improving the cosmetic appeal or aesthetics of the appliance. Finally, when using light-cure adhesive or cement, inasmuch as the bonding base or pad now is either optically clear or translucent, penetration of the curing light between the metal appliance body and the tooth enamel surface is substantially greater thereby substantially increasing the bond strength of the appliance to a tooth. This decreases the possibility of loosening during the treatment process.

According to the present invention, the method employed in making an orthodontic appliance, which includes a body of metal, ceramic or plastic having a buccal/labial archwire receiving side and a lingual side, includes preparing the appliance body and molding a polymer resin bonding base onto the lingual side of the body such that at least part of the body is embedded in the base. At least one opening extending therethrough may be molded in the base for receiving an anchoring arm of an auxiliary appliance or a secondary archwire.

The method of making an orthodontic appliance according to the invention includes the steps of first making an orthodontic appliance body of metal, ceramic or plastic, cleaning the surface of the appliance body where needed, subjecting the body to an adhesion-promoting process, and then molding either a light-curable or heat-curable polymer resin bonding base onto the lingual side of the body that may have at least one opening extending through the body thereby defining a one-piece orthodontic appliance. The polymer resin base may be acrylic, epoxy, or epoxy/acrylic in the form of an acrylic-based epoxy, and which is either light curable or heat curable.

Another embodiment of the invention is to form the orthodontic appliance of an appliance body and a polymer resin bonding base molded onto the body, and providing the appliance body and bonding base with matching grooves that coact to form a vertical slot or opening.

It is therefore an object of the present invention to provide an orthodontic appliance of the bracket or tube type from a standard bracket or tube appliance body and a polymer resin base with or without openings in the base to thereby reduce manufacturing costs associated with making one appliance without openings and another with openings.

Another object of the present invention to provide an orthodontic appliance including an appliance body of metal, ceramic or plastic and a heat or light-curable polymer resin bonding base molded onto the body and having at least one opening extending therethrough for receiving an arm of an auxiliary appliance or a secondary archwire.

A further object of the present invention is to provide an orthodontic appliance including an appliance body and a polymer resin bonding base molded to the body having at least one opening through the base for receiving an auxiliary or a secondary archwire.

A still further object of the present invention is to provide an orthodontic appliance having a metal appliance body and a polymer resin bonding base molded to the body that reduces the in-out compensation and the profile height of the appliance, and wherein the polymer resin bonding base may be optically clear or translucent to enhance the aesthetics of the appliance.

A still further object of the present invention is to provide an orthodontic appliance having a metal appliance body and a polymer resin bonding base molded to the body that reduces the in-out compensation and the profile height of the appliance, and wherein the polymer resin bonding base may be optically clear or translucent to increase the bond strength when bonded to a tooth with a light-cure adhesive.

Other objects, features and advantages will be apparent from the following detailed disclosure taken in conjunction with the accompanying sheets of drawings where like reference numerals refer to like parts.

DESCRIPTION OF THE INVENTION

Figure 1:
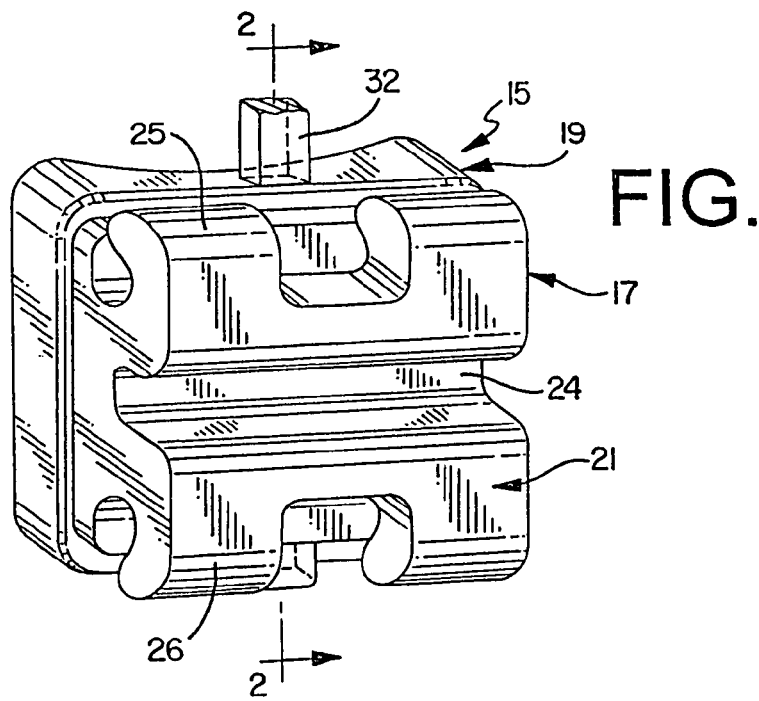
FIG. 1 is a perspective view of an orthodontic appliance according to the present invention including an appliance body having a polymer resin bonding base molded to the body with a vertical opening through the bonding base.

The present invention relates to a bondable orthodontic appliance having a polymer resin base or pad. The orthodontic appliance includes an appliance body having the polymer resin base or pad molded to the body. While the drawings show the appliance body as a bracket having an archwire receiving side and a lingual side, it should be appreciated that the appliance body may be in the form of a buccal tube which also has an archwire receiving side and a lingual side. Also, while the appliance body illustrated in the drawings is in the form of an edgewise bracket having a substantially horizontally extending open archwire receiving slot and ligature receiving tie wings, it should be appreciated that the appliance body may have one or more sets of tie wings, or it may have an appliance body of the self-ligating type. Further, the appliance body may be formed for mounting on the buccolabial surface of a tooth or on the lingual surface of a tooth.

Where the appliance body is in the form of a molar tube, it will be appreciated that any type of a molar tube configuration may be used.

It should also be appreciated that the appliance body, while having a polymer resin base or pad molded to the body, may be of any suitable material such as ceramic, metal or plastic of the types heretofore known. For example, according to the invention an orthodontic appliance could include a ceramic appliance body onto which the polymer resin base or pad is molded to define a bondable orthodontic appliance. Also, the appliance body could be of metal with a polymer resin base molded onto the lingual side of the body. Finally, the appliance body could be made of a suitable plastic such as a polycarbonate and have a polymer resin base or pad molded onto the lingual side of the base or body.

It should also be appreciated that the polymer resin employed for making the base or pad may be an acrylic resin, an epoxy resin, an epoxy/acrylic resin (acrylic-based epoxy), or any other suitable moldable polymer resin capable of bonding to the lingual side of an appliance body to provide the bond strength to resist separation during use and also be compatible with a bonding adhesive or cement. It should also be appreciated that the polymer resin may be heat-curable or light-curable, although it is preferably light-curable.

Figure 2:
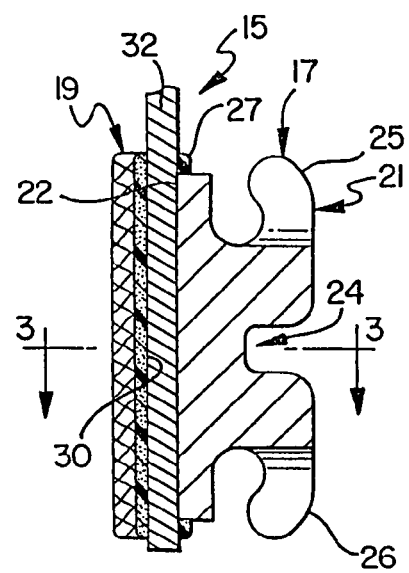
FIG. 2 is a vertical sectional view taken through the bracket of FIG. 1 and substantially along line 2-2 thereof.
Figure 3:
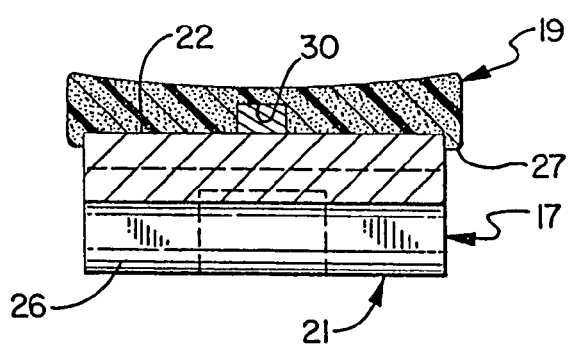
FIG. 3 is a horizontal sectional view taken through the bracket of FIG. 2 and substantially along line 3-3 thereof.

Referring now to the embodiment of FIGS. 1 to 3, an orthodontic appliance, generally indicated by the numeral 15 according to the invention, includes an appliance body 17 and a polymer resin base or pad 19.

The appliance body 17 includes an archwire receiving side 21 and a lingual side 22. In the illustrated embodiment, the archwire receiving side of the body 17 includes a horizontally extending and buccolabially opening archwire slot 24 and upper and lower tie wings 25 and 26. As above mentioned, the archwire receiving side of the appliance body may take any number of forms including but not limited to the Tip-Edge Bracket sold by TP Orthodontics, Inc. "Tip-Edge" is a trademark owned by TP Orthodontics, Inc. Moreover, as above mentioned, the material of the appliance body may be ceramic, metal or plastic.

The polymer resin base 19, as above noted, may be of any suitable resin, including an acrylic resin, an epoxy resin, or an acrylic-based epoxy resin, which is molded to the lingual side 22 of the appliance body such that at least part of the lingual side of the appliance body is embedded in the polymer resin base to enhance the bond strength, as seen by the peripheral lip 27, shown most clearly seen in FIGS. 2 and 3, where the lip overlaps a part of the appliance body to assure that the base is properly bonded to the appliance body to withstand the forces applied to the appliance body by the main archwire and/or an auxiliary or secondary archwire during use by a patient.

When molding the polymer resin base onto the appliance body, an opening or slot 30 may be molded into the base by placement of a suitable form in the resin before curing. In this embodiment, the opening 30 extends vertically and particularly for receiving an arm 32 of an auxiliary. While the cross-sectional shape of the arm 32 is shown to be rectangular, it should be appreciated it could be round or of another cross-sectional shape. Moreover, the opening 30 could likewise have a round cross section or some other cross section. In the embodiment illustrated, a part of the opening is formed by the lingual surface of the appliance body 17, although it could be totally formed in the base. The bondable face of the base 19 is preferably arcuate as illustrated in order to conform to an arcuate surface of a tooth. Further, the outer periphery of the base being greater than the outer periphery of the appliance facilitates the transmission of a curing light when bonding the appliance to a tooth with a light-cure adhesive.

As also mentioned above, the polymer resin after being molded onto the lingual side of an appliance body would be heat-cured if the resin is of the heat-curable type or light-cured if the resin is of a light-curable type.

Further, where it would be desired to omit the vertical opening for an auxiliary arm, the vertical opening would not be molded into the base during the molding of the base on to the lingual side of the appliance body.

With respect to the embodiment of FIGS. 1 to 3, as well as the other embodiments of the invention, and whether the appliance body is a bracket or a molar tube, it will be appreciated that the appliance body is suitably prepared prior to molding the base onto the body so as to provide the best possible bond between the base and body.

With respect to the method of making an appliance with a metal or ceramic appliance body, the appliance body is first cleaned and polished and the surface of the body is activated to enhance the bond strength between the polymer resin base and the body. Activation of the appliance body includes dipping the body in a silane solution, curing the silane coating with heat, and then coating the appliance body with an acrylic polymer solution. After applying this coating, the coating is suitably cured and this coating process promotes the adhesion between the polymer resin and the appliance body when molding the polymer resin base onto the body. Thus, the bond strength between the base and the body is substantially increased to inhibit separation of the base from the body during use.

Where the appliance body is ceramic and a bracket, a metallic oxide is included in the polymer resin, as disclosed in co-pending application Ser. No. 10/120,052 filed Apr. 10, 2002, now U.S. Pat. No. U.S. Pat. No. 6,786,720, and also owned by the assignee of this application.

Where the appliance body is a bracket of metal, the polymer resin may be optically clear or translucent to allow penetration of the curing light beneath the appliance body and enhance the bonding of a light-cure adhesive used to bond the appliance to a tooth.

It should be further appreciated that inasmuch as the polymer resin base is molded to the lingual side of the appliance body and with a curvature to match that of a tooth, the lingual side of the appliance body need not have a curvature and may be planar in shape which will facilitate the manufacture of the appliance body.

It should further be appreciated that the orthodontic appliance with the polymer resin base may be bonded to a tooth chemically or mechanically and that the bonding surface of the base will preferably be roughened or formed with undercuts or a mesh-like structure to further enhance the bond strength of the adhesive or cement used to bond the appliance to a tooth. Preferably, a light-cured adhesive would be used, the curing of which is facilitated by the optically clear or translucent polymer resin base of the appliance of the invention.

The appliance is made by first making an orthodontic appliance body having an archwire receiving side and a lingual side. The polymer resin is injected into a cavity having the desired shape of the base. The appliance body is then placed into the resin such that part of the body is under the level of the resin to produce an appliance with part of the lingual side being embedded in the body. Suitable forms would be placed in the resin to mold one or more openings in the base if an opening is desired. The resin would then be cured to complete the base formation step.

Figure 4:
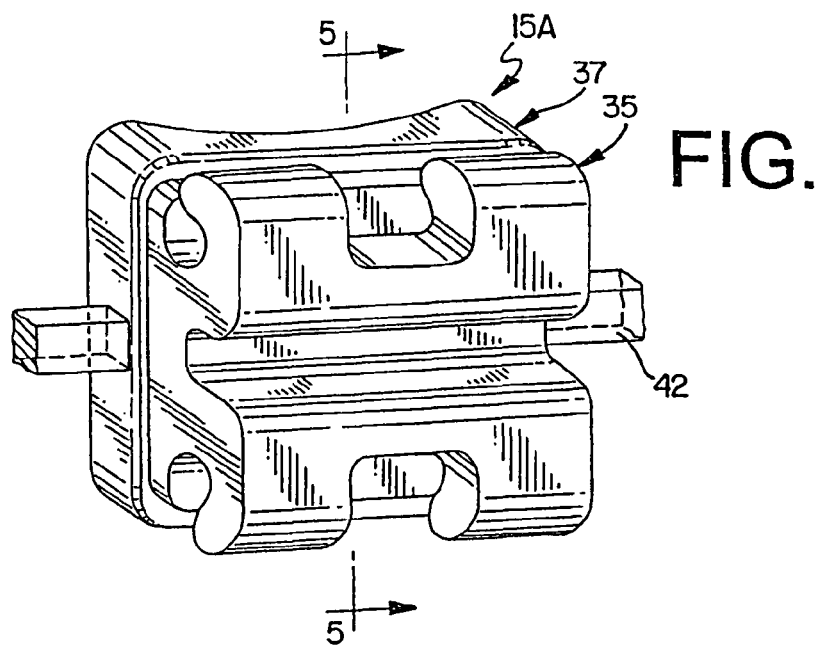
FIG. 4 is a perspective view of a bracket and bonding pad like that of FIG. 1 but illustrating the opening through the bonding base to be extending horizontally.
Figure 5:
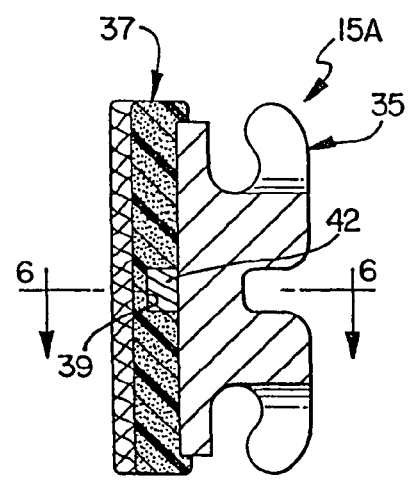
FIG. 5 is a vertical sectional view taken through the appliance of FIG. 4, and substantially along line 5-5 thereof.
Figure 6:
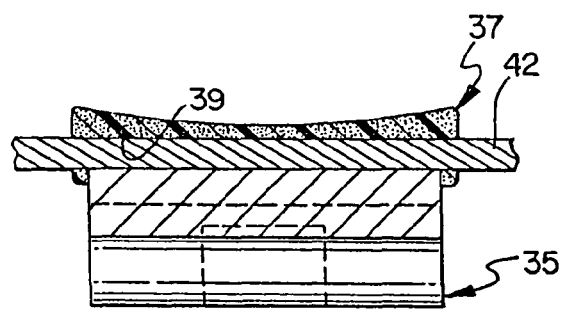
FIG. 6 is a horizontal sectional view taken through the bracket of FIG. 5, and substantially along the line 6-6 thereof.

Referring now to the embodiment of FIGS. 4, 5 and 6, an orthodontic appliance, generally indicated by the numeral 15A, differs from the embodiment of FIGS. 1 to 3 only in that the opening or slot in the base extends horizontally instead of vertically. This embodiment includes in general an appliance body 35 of the same type illustrated in the embodiment of FIGS. 1 to 3 and a polymer resin base 37 provided with a horizontally extending opening 39 at the lingual side of the appliance. As in the embodiment of FIGS. 1 to 3, the cross-sectional shape of the opening is rectangular and one side of the opening may be of any suitable cross-sectional shape. In this embodiment the horizontally extending opening in the base may receive a secondary archwire 42 as shown. When molding the base on a Tip-Edge Bracket body, and including a horizontal opening, the opening can also accommodate a leveling archwire, as described in the co-pending application Ser. No. 10/177,951, now U.S. Pat. No. 6,682,345, filed Jun. 21, 2002, also owned by the assignee of this application.

Figure 7:
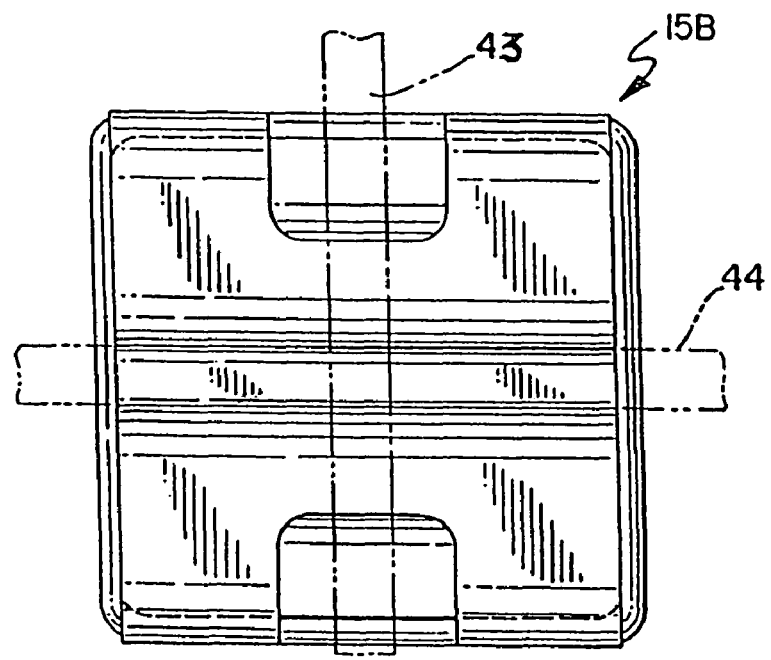
FIG. 7 is a front elevational view of further modified bracket of the invention and illustrating in phantom both vertically and horizontally extending openings in the base.

It will be further understood that multiple openings or slots may be formed in the polymer resin base if desired, and such an embodiment is shown in FIG. 7, wherein the appliance is generally indicated by the numeral 15B. This appliance includes a vertical opening that can be utilized for an anchoring arm 43 of an auxiliary, as shown in phantom, or a horizontal opening for a secondary archwire 44 that is shown in phantom.

Figure 8:
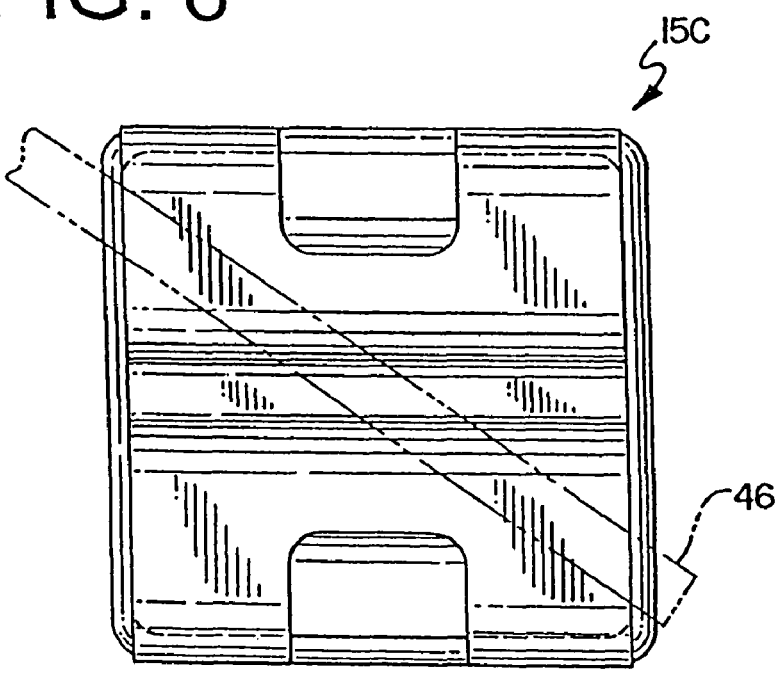
FIG. 8 is a front elevational view of a further modified bracket of the invention and illustrating in phantom a diagonally extending opening in the base.
Figure 9:
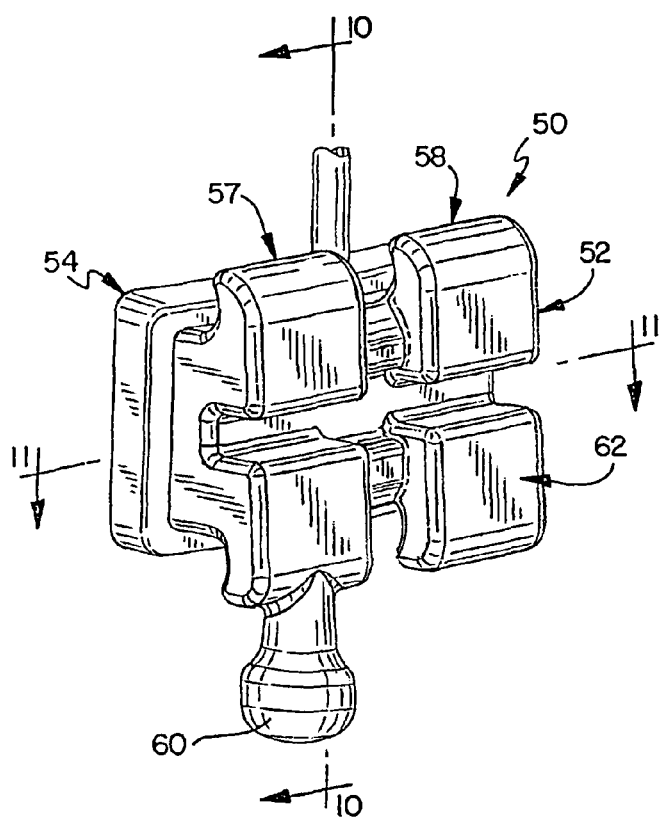
FIG. 9 is a perspective view of a still further modified bracket of the invention showing a vertically extending opening that is formed by matching grooves in the base and the appliance body.
Figure 10:
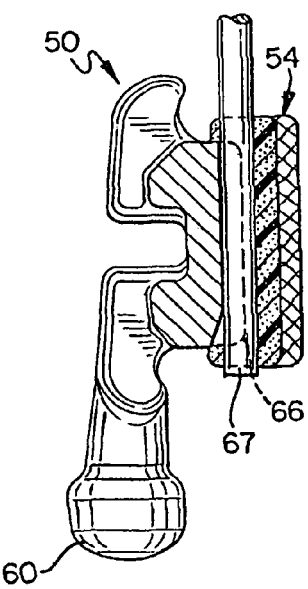
FIG. 10 is a vertical sectional view taken substantially along line 10-10 of the bracket in FIG. 9.
Figure 11:
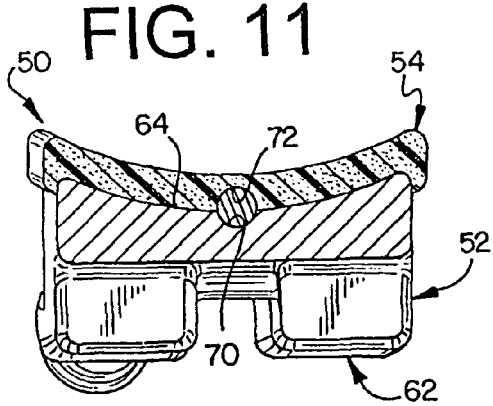
FIG. 11 is a horizontal sectional view taken substantially along line 11-11 of the appliance of FIG. 9.
Figure 12:
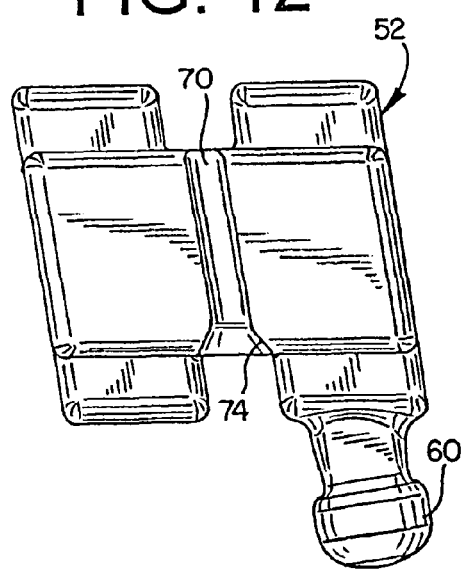
FIG. 12 is a rear or back side view of the bracket body of the embodiment of FIGS. 9 to 11 prior to molding a bonding base on the bracket body to illustrate the groove formed in the bracket body that coacts with the groove formed in the polymer resin bonding base during molding the base on the bracket body.

As previously mentioned, the opening in the base may even extend diagonally, as illustrated in the appliance indicated by the numeral 15C in FIG. 8. In this embodiment, a diagonal opening is formed in the base to receive a diagonally extending arm 46 of a suitable auxiliary. The angle of the opening relative to the vertical axis of the appliance may be selected in accordance with the desired function to be employed with the particular appliance and an auxiliary.

Referring now to FIGS. 9 to 12, a further orthodontic appliance according to the invention is shown and generally designated by the numeral 50, and which generally includes an appliance body 52 and a polymer resin base 54. While the appliance body 52 is of a different form than those shown in the embodiments of FIGS. 1 to 8, this embodiment differentiates primarily from the other embodiments in that the opening for receiving an arm of an auxiliary is formed by matching grooves in the appliance body and the base. Further, the appliance body is of the true twin tie wing type and includes tie wings 57 and 58, each of which includes upper and lower tie wing tips. Additionally, the lower tie wing tip of the tie wing 57 includes a ball hook 60.

The appliance body 52 includes an archwire receiving side 62 and a lingual side 64 to which the polymer resin base 54 is molded, as previously explained with the other embodiments.

The lingual side 64 of the appliance body 52 is arcuately formed in accordance with the expected curvature of the tooth on which it would be mounted. Similarly, the polymer resin base 54 includes an arcuately formed lingual surface to conform to the surface of a tooth on which is it mounted. As in the other embodiments, the bonding face of the base may have a mesh-like surface in order to enhance the bonding to a tooth.

A vertically extending opening, generally designated by the numeral 66, for receiving an arm 67 of an auxiliary is formed by matching grooves in the appliance body and the base. A groove 70 is formed in the appliance body, while a groove 72 is formed in the base, which together coact to define the vertical opening 66. During the molding of the base onto the lingual side of the appliance body, a suitable pin is laid in the groove 70 of the appliance body and which then forms the groove 72 in the base to produce the opening 66. Preferably, the lower end of the groove 70 is flared at 74 and similarly the lower end of the groove 72 of the base would be flared to provide a flared opening for facilitating the insertion of an arm of an auxiliary. Similarly, the upper end of the grooves might be flared if so desired.

It will be understood that modifications and variations may be effected without departing from the scope of the novel concepts of the present invention, but it is understood that this application is to be limited only by the scope of the appended claims.

The invention is hereby claimed as follows:

1. An orthodontic appliance for shipment to a user including a metal appliance body having a buccal/labial archwire receiving side and a lingual side, said archwire receiving side of said body including at least one tie wing having a labial profile, and said lingual side of said body including a base portion having a lingual profile, a connecting portion between the base portion on the lingual side and the tie wing, the lingual profile of the base portion being substantially equal to the labial profile of the tie wing, and a light-permeable, heat or light-cured polymer resin bonding base molded onto the lingual of said base portion of said body and including an integral peripheral lip overlapping a part of the base portion to enhance the bonding of the bonding base to the base portion of said body and having substantially the same lingual profile as the lingual profile of said base portion wherein the light-permeable base enhances the use of and curing of a light-cure adhesive by allowing the curing light to penetrate beneath the appliance when bonding the appliance to a tooth to substantially increase the bond strength of the appliance on a tooth.

2. The orthodontic appliance of claim 1, wherein the polymer resin base is acrylic, epoxy or acrylic-based epoxy.

3. The orthodontic appliance of claim 1, wherein the appliance is a bracket or a tube.

4. A method of making an orthodontic appliance for shipment to a user including a body of ceramic, metal, or plastic having a buccal/labial archwire receiving side and a lingual side, and said archwire receiving side of said body including at least one tie wing having a labial profile, and said lingual side of said body including a base portion having a lingual profile, a connecting portion between the base portion on the lingual side and the tie wing, the lingual profile of the base portion being substantially equal to the labial profile of the tie wing, a light-permeable polymer resin bonding base molded onto the lingual of said base portion of said body and including an integral peripheral lip overlapping part of the base portion to enhance the bonding base to the base portion of said body and having substantially the same lingual profile as the lingual profile of said base portion said method comprising the steps of:

making an orthodontic appliance body of ceramic, metal, or plastic of one size such that when a bondable light-permeable polymer resin base is molded to the lingual side of the body the base includes an integral peripheral lip overlapping a part of the appliance body, wherein a bondable orthodontic appliance is produced for shipment to a user for bonding to a tooth, and said body having an archwire receiving side and a lingual side on which the base is molded, and molding a light-permeable, light-curable or heat-curable polymer resin bonding base to the lingual of said base portion of said body such that the lingual side at least partially overlaps the base and a peripheral lip is formed at the perimeter of the appliance body thereby enhancing the bonding of the bonding base to the base portion of said body wherein the light-permeable base enhances the use of and curing of a light-cure adhesive by allowing the curing light to penetrate beneath the appliance when bonding the appliance to a tooth to substantially increase the bond strength of the appliance on a tooth.

5. An orthodontic appliance for shipment to a user including an appliance body of metal, ceramic, or plastic, having a buccal/labial archwire receiving side and a lingual side, said archwire receiving of said body including at least one tie wing having a labial profile, and said lingual side of said body including a base portion having a lingual profile, a connecting portion between the base portion on the lingual side and the tie wing, the lingual profile of the base portion being substantially equal to the labial profile of the tie wing, a light-permeable, heat or light-cured polymer resin bonding base molded onto the lingual of said base portion of said body and including an integral peripheral lip overlapping a part of the appliance body, said integral peripheral lip assuring the base portion to enhance the bonding of the bonding base to the base portion of said body and having substantially the same lingual profile as the lingual profile of said base portion to withstand the forces applied to the body by an archwire during use by a patient, and said appliance further including a first groove formed in said appliance body and a second groove formed in said base coacting with said first groove to define an opening for receiving an arm of an auxiliary appliance or a secondary archwire for applying a predetermined force to a tooth on which the appliance may be mounted, wherein the light-permeable base enhances the use of and curing of a light-cure adhesive by allowing the curing light to penetrate beneath the appliance when bonding the appliance to a tooth to substantially increase the bond strength of the appliance on a tooth.

* * * * *

UNITED STATES PATENT AND TRADEMARK OFFICE
CERTIFICATE OF CORRECTION

| | |
|---|---|
| PATENT NO. | : 7,780,442 B2 |
| APPLICATION NO. | : 10/695695 |
| DATED | : August 24, 2010 |
| INVENTOR(S) | : Andrew C. Kesling |

It is certified that error appears in the above-identified patent and that said Letters Patent is hereby corrected as shown below:

Col. 8, line 50, after "bonding" insert --of the bonding--; and
Col. 9, line 12, after "receiving" insert --side--.

Signed and Sealed this

Fourteenth Day of December, 2010

David J. Kappos
*Director of the United States Patent and Trademark Office*